US00PP19877P2

(12) United States Plant Patent
Bullis

(10) Patent No.: US PP19,877 P2
(45) Date of Patent: Mar. 31, 2009

(54) ***AECHMEA* PLANT NAMED 'FANTASY'**

(50) Latin Name: *Aechmea chantinii*
Varietal Denomination: Fantasy

(75) Inventor: Patricia Gomez Bullis, Princeton, FL (US)

(73) Assignee: Bulllis Bromeliads, Princeton, FL (US)

( * ) Notice: Subject to any disclaimer, the term of this patent is extended or adjusted under 35 U.S.C. 154(b) by 0 days.

(21) Appl. No.: 12/005,101

(22) Filed: Dec. 20, 2007

(51) Int. Cl.
*A01H 5/003* (2006.01)

(52) U.S. Cl. ..... Plt./370

(58) Field of Classification Search ..... Plt./370
See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Aechmea* plant named 'Fantasy', characterized by its upright and outwardly arching growth habit; unique white, light green and green variegated foliage with green-colored margins and white, light green and green-colored longitudinal stripes; inflorescences held upright and above foliage on strong scapes; tightly branched inflorescences with red-colored flower bracts; and long-lasting inflorescences.

3 Drawing Sheets

Botanical designation: *Aechmea chantinii.*
Cultivar denomination: 'FANTASY'.

BACKGROUND OF THE INVENTION

The present invention relates to a new and distinct cultivar of *Aechmea,* botanically known as *Aechmea chantinii* and hereinafter referred to by the name 'Fantasy'.

The new *Aechmea* is a naturally-occurring whole plant mutation of the *Aechmea chantinii* cultivar Fantasia, not patented. The new *Aechmea* was discovered and selected by the Inventor from within a population of plants of 'Fantasia' in a controlled greenhouse environment in Princeton, Fla. in May, 2003. The new *Aechmea* was selected based on its unique variegated leaves; plants of the cultivar Fantasia have solid green-colored leaves.

Asexual reproduction of the new *Aechmea* by offsets in a controlled environment in Princeton, Fla. since June, 2004, has shown that the unique features of this new *Aechmea* are stable and reproduced true to type in successive generations.

SUMMARY OF THE INVENTION

The cultivar Fantasy has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fantasy'. These characteristics in combination distinguish 'Fantasy' as a new and distinct cultivar of *Aechmea:*

1. Upright and outwardly arching growth habit.
2. Unique white, light green and green variegated foliage with green-colored margins and white, light green and green-colored longitudinal stripes.
3. Inflorescences held upright and above foliage on strong scapes.

4. Tightly branched inflorescences with red-colored flower bracts.
5. Long-lasting inflorescences.

Plants of the new *Aechmea* differ from plants of the parent, the cultivar Fantasia, primarily in leaf color as plants of the cultivar Fantasia have solid green-colored leaves.

Plants of the new *Aechmea* can be compared to plants of the cultivar Harvey's Pride, disclosed in U.S. Plant Pat. No. 12,075. Plants of the new *Aechmea* and the cultivar Harvey's Pride differ primarily in leaf color as plants of the cultivar Harvey's Pride have yellow and green variegated foliage.

BRIEF DESCRIPTION OF THE PHOTOGRAPHS

The accompanying colored photographs illustrate the overall appearance of the new *Aechmea,* showing the colors as true as it is reasonably possible to obtain in colored reproductions of this type. Colors in the photographs may differ slightly from the color values cited in the detailed botanical description which accurately describe the colors of the new *Aechmea.*

The photograph on the first sheet is a side perspective view of a typical flowering plant of 'Fantasy' grown in a container.

The photograph on the second sheet is a close-up view of a typical inflorescence of 'Fantasy'.

The photograph on the third sheet is a top perspective view of a typical inflorescence of 'Fantasy'.

DETAILED BOTANICAL DESCRIPTION

The aforementioned photographs and following observations, measurements and values describe plants grown in Princeton, Fla. during the spring and summer under commercial practice in a polypropylene-covered shade house with day temperatures averaging 31° C. and night temperatures averaging 18° C. The polypropylene shade cloth provided a 74 percent decrease in ambient light levels. Single plants used for the photographs and description were about 14 months old and grown in 23-cm containers. In the following description, color references are made to The Royal Horticultural Society Colour Chart, 1995 Edition, except where general terms of ordinary dictionary significance are used.

Botanical classification: *Aechmea chantinii* cultivar Fantasy.

Parentage: Naturally-occurring whole plant mutation of the *Aechmea chantinii* cultivar Fantasia, not patented.

Propagation:

*Type.*—By offsets.

*Time to initiate roots.*—About two to three weeks.

*Time to produce a rooted young plant.*—About four months.

*Root description.*—Medium in thickness, fibrous; white to brown in color.

*Rooting habit.*—Moderately freely branching; medium density.

Plant description:

*General appearance.*—Upright and outwardly arching growth habit. Rosette leaves are erect when young, becoming outwardly arching with development. Plants readily produce offsets.

*Crop time.*—From offsets, typically about 11 to 14 months are required to produce flowering finished plants in 23-cm containers; vigorous growth habit.

*Plant height, soil surface to top of leaf canopy.*—About 64 cm.

*Plant height, soil surface to top of inflorescence.*—About 87 cm.

*Plant diameter or spread.*—About 76 cm.

Foliage description:

*Arrangement.*—Rosette, spiral phyllotaxis.

*Shape.*—Linear.

*Apex.*—Cuspidate.

*Margin.*—Entire with very sharp spines.

*Length.*—About 51 cm.

*Width.*—About 7.6 cm.

*Aspect.*—Concave.

*Texture.*—Upper and lower surfaces, smooth; glabrous; leathery; thick; lower surface, glaucous.

*Color.*—Young and mature leaves, upper surface: Towards the margins, more green than 146A; central parallel longitudinal stripes, 146A, 144A, 154A and close to 158A. Young and mature leaves, lower surface: Towards the margins, 146A; central parallel longitudinal stripes, 146A, 144A and close to 158A.

Inflorescence description:

*Inflorescence form.*—Large terminal inflorescences arranged in tightly branched and spirally twisting lateral panicles supported by erect and strong scapes. About 24 lateral panicles each with about 22 individual flowers. Flowers ovoid in shape; bright red, white and yellow flower bracts.

*Inflorescence longevity.*—Inflorescences of the new *Aechmea* are very long-lasting; typically bract color will be maintained for about two to four months.

*Inflorescence size.*—Length: About 31 cm. Width: About 26 cm.

*Lateral panicle size.*—Length: About 11 cm. Diameter: About 4 cm.

*Flower size.*—Length: About 2.5 cm. Diameter: About 1 cm.

*Primary bracts.*—Arrangement: Subtend each panicle. Shape: Linear. Length: About 10.5 cm. Width: About 3.4 cm. Texture: Glaucous. Color: Close to 53A to 53C.

*Flower bracts.*—Arrangement: Closely adhered to sepals. Shape: Elongate, sharply acuminate. Length: About 2.5 cm. Width: About 1.2 cm. Texture: Smooth. Color: Initially yellow green, 154A, becoming bright yellow, 9A, then red, close to 53A to 53C, starting at the base.

*Petals.*—Appearance: Not united, usually with two scales inside of sepals. Color: Close to 154A. Scape: Strength: Very strong. Aspect: Typically erect. Length: About 87 cm. Diameter: About 1.25 cm. Texture: Sticky, glaucous. Color: Close to 53C to 53D. Reproductive organs: Inconspicuous. Seed: Seed production has not been observed.

Temperature tolerance: Plants of the new *Aechmea* have been observed to tolerate temperatures ranging from about 9° C. to about 35° C.

Disease/pest resistance: Resistance to pathogens and pests common to *Aechmea* has not been observed.

It is claimed:

1. A new and distinct *Aechmea* plant named 'Fantasy' as illustrated and described.

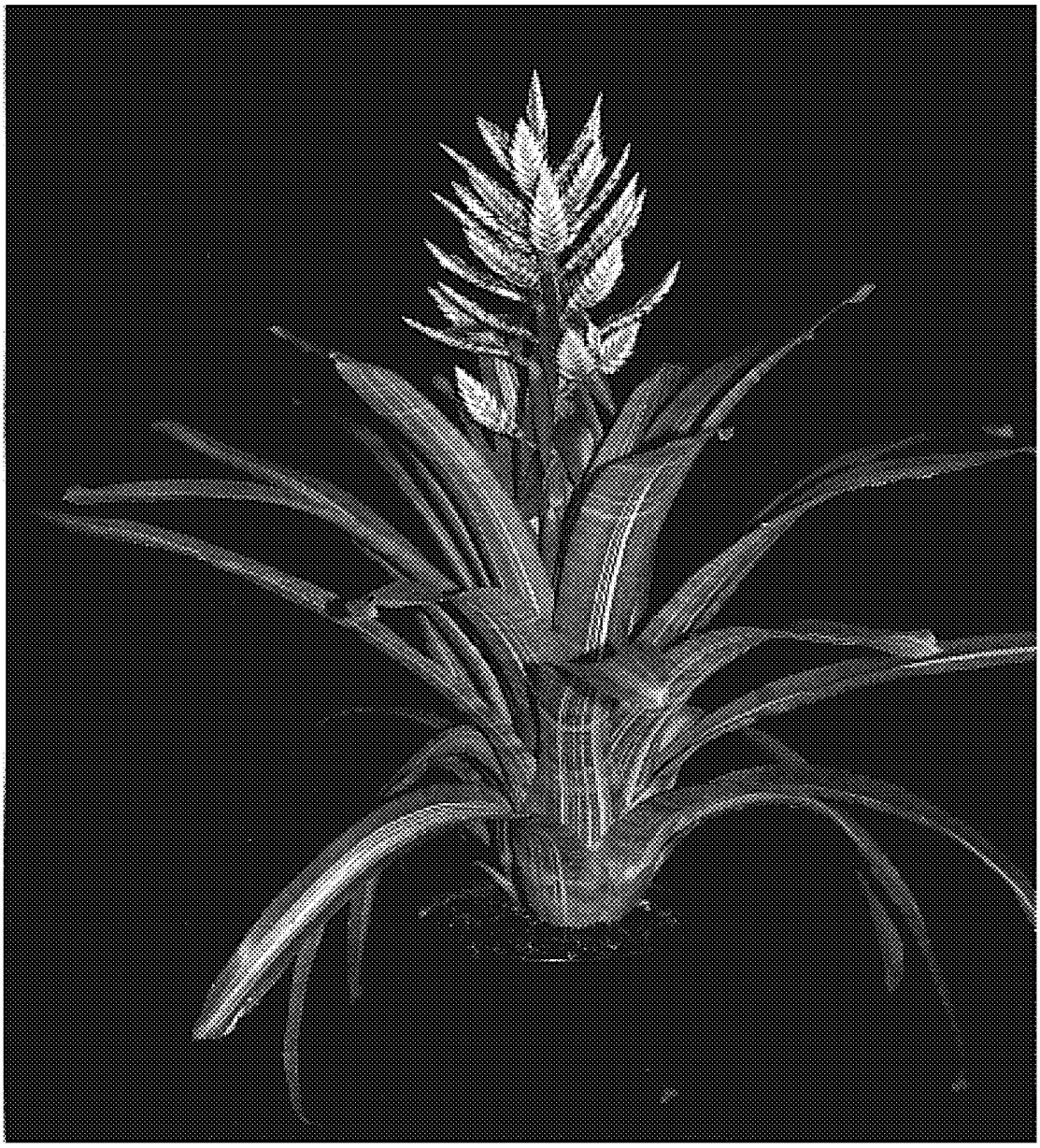

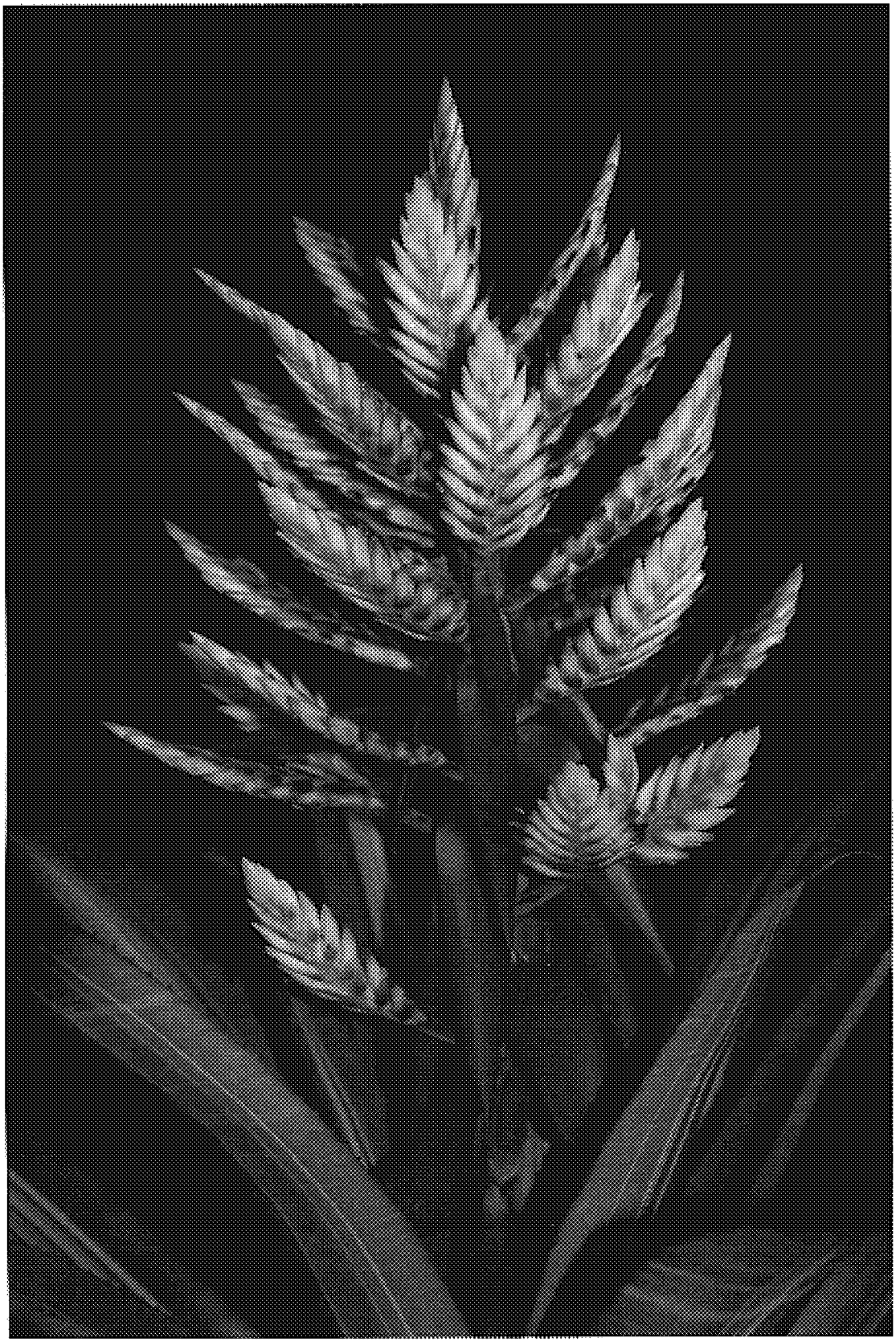

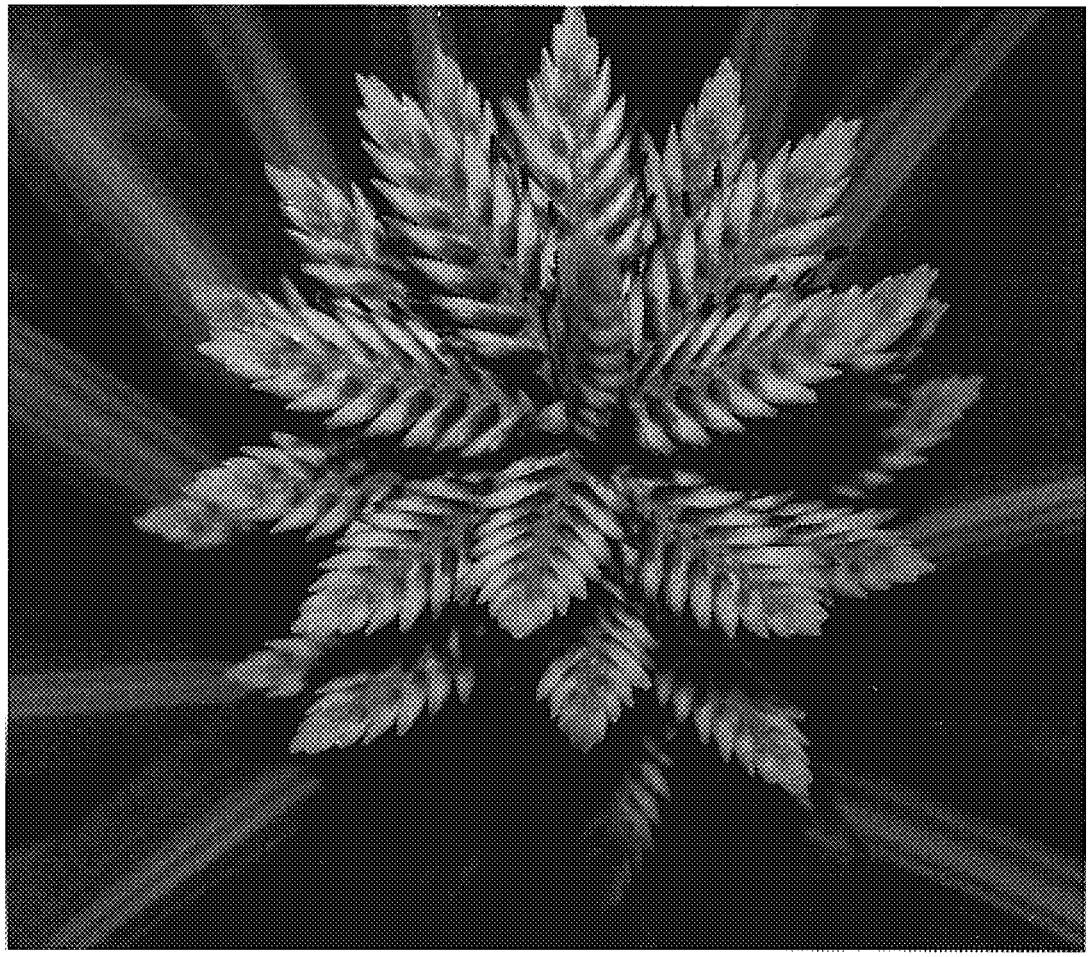

* * * * *